United States Patent
Allen et al.

(10) Patent No.: US 6,789,944 B1
(45) Date of Patent: Sep. 14, 2004

(54) SANITARY HANDGRIP COVER

(76) Inventors: Richard Allen, 10 Ranick Rd., Hauppauge, NY (US) 11788; Mitchell Steinberg, 10 Ranick Rd., Hauppauge, NY (US) 11788

( * ) Notice: Subject to any disclaimer, the term of this patent is extended or adjusted under 35 U.S.C. 154(b) by 45 days.

(21) Appl. No.: 10/390,276

(22) Filed: Mar. 18, 2003

(51) Int. Cl.[7] ............................................. B65D 30/10
(52) U.S. Cl. ............................ 383/35; 383/66; 150/154
(58) Field of Search ............. 383/66, 35; 150/154–156, 150/160–161, 165

(56) References Cited

U.S. PATENT DOCUMENTS

| | | | | |
|---|---|---|---|---|
| 465,649 A | * | 12/1891 | Roberts | 206/815 |
| 3,051,304 A | * | 8/1962 | Dogorukov | 206/371 |
| 3,072,167 A | * | 1/1963 | Banas | 150/160 |
| 3,411,698 A | * | 11/1968 | Reynolds | 383/35 |
| 3,782,434 A | * | 1/1974 | Lebherz | 383/40 |
| 3,979,050 A | * | 9/1976 | Cilia | 383/35 |
| 4,119,129 A | * | 10/1978 | Freiberg | 150/160 |
| 4,652,239 A | | 3/1987 | Brimberg | |
| 4,871,046 A | * | 10/1989 | Turner | 181/131 |
| 5,907,877 A | * | 6/1999 | Allgood | 5/649 |
| 6,467,568 B1 | * | 10/2002 | Kemper | 181/131 |

* cited by examiner

*Primary Examiner*—Jes F. Pascua
(74) *Attorney, Agent, or Firm*—Myron Amer, P.C.

(57) ABSTRACT

In a bag configuration, a sanitary cover of clear plastic construction material to be placed over a handgrip of a dentist's overhead light that has an imprint, such as an arrow, on a rear bag panel in the middle of unsealed edges that in use bound an opening through which the handgrip is projected into the bag, in which the user is instructed to rub apart the unsealed edges at the observed site of the arrow, and thus neutralizes a static electricity clinging together of the unsealed edges that otherwise would be difficult to separate.

2 Claims, 2 Drawing Sheets

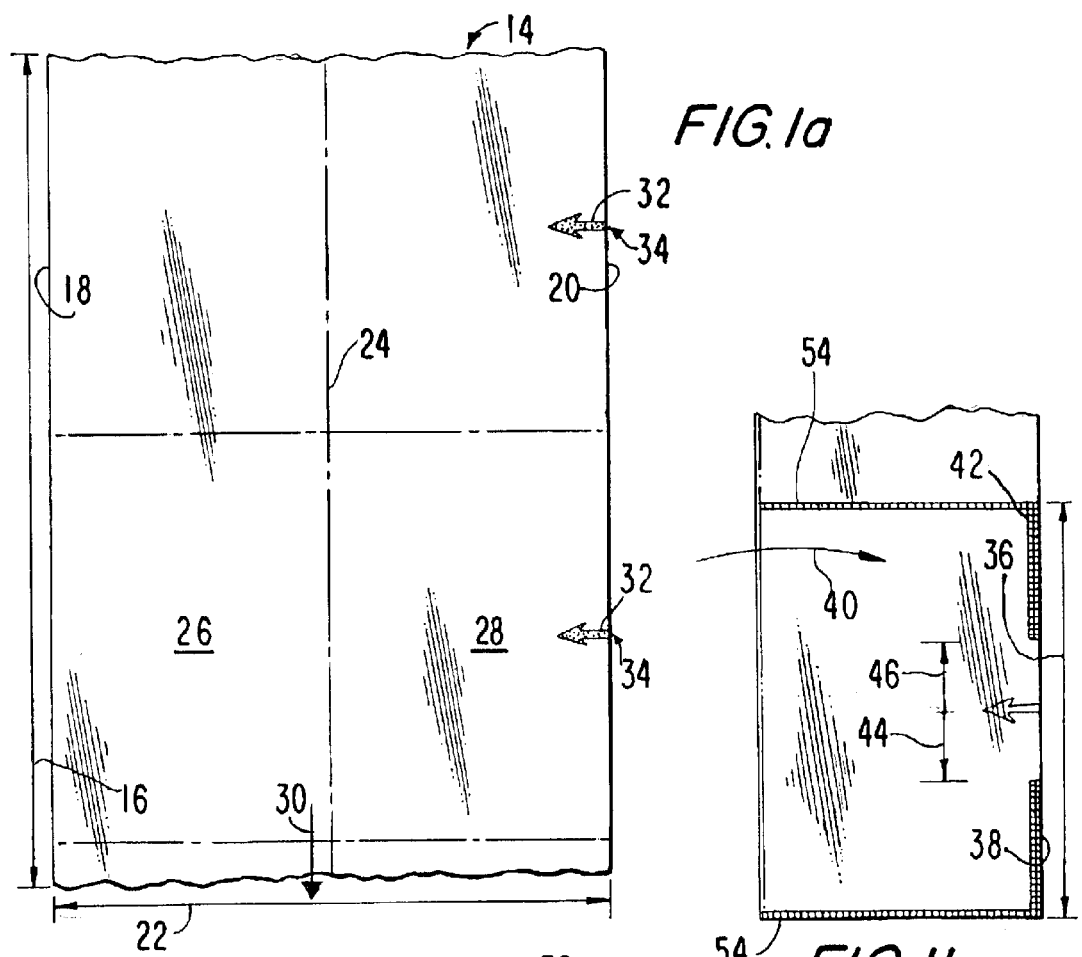
FIG. 1a
FIG. 1b
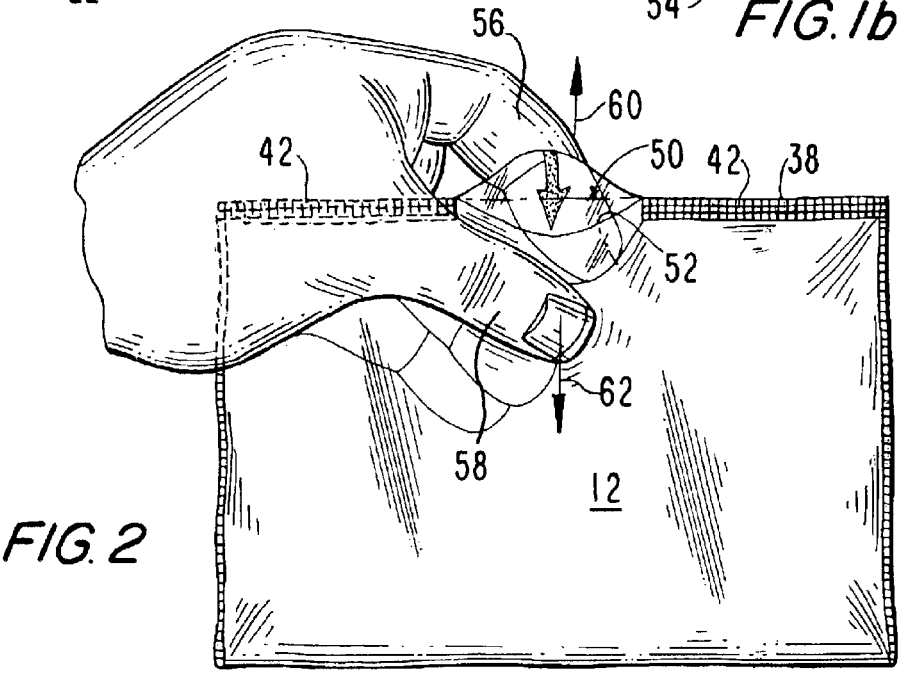
FIG. 2

SANITARY HANDGRIP COVER

In dentistry in particular, great precautions are taken to prevent the transmission of disease from one patient to another, and the present invention contributes significantly to the continuance of this practice.

EXAMPLE OF THE PRIOR ART

In sanitizing dental treatments, the material of choice is plastic as exemplified by the use of plastic as the construction material of disposable gloves, head covers, aprons and the like. However, a drawback is that in the manufacture and handling of plastic it takes on a static electricity charge complicating the separation of plies, a phenomenon described and illustrated in U.S. Pat. No. 4,652,239 for "Space Planning System and Method" issued to Brimberg on Mar. 24, 1987. The static cling is of minor consequence in the use of gloves and other provided protections, but this is not so in all instances, such as the placement of a sanitary cover on the handgrip of a dentist's overhead light.

Broadly, it is an object of the present invention to provide a plastic sanitary handgrip cover for a dentist's overhead light overcoming the foregoing and other shortcomings of the prior art.

More particularly, it is an object to embody guides to a user on the sanitary handgrip cover to neutralize the static electric charge to correspondingly facilitate placement of the cover on the handgrip, all as will be better understood as the description proceeds.

The description of the invention which follows, together with the accompanying drawings should not be construed as limiting the invention to the example shown and described, because those skilled in the art to which this invention appertains will be able to devise other forms thereof within the ambit of the appended claims.

FIGS. 1a and 1b are illustrations, in plan perspective, of successive steps in the heat sealing fabrication of plastic construction material into the sanitary cover for a handgrip of a dentist's overhead light according to the present invention;

FIG. 2 is an isolated plan view of the sanitary cover and an illustration of its preparation for use.

Figure 3:
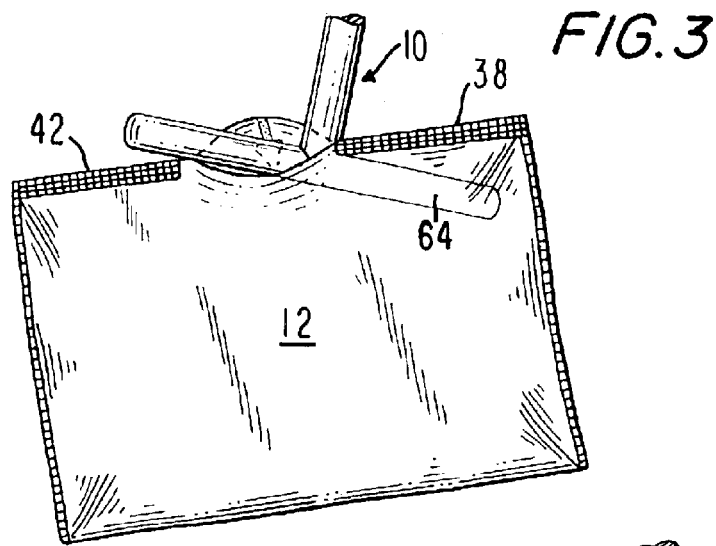
FIGS. 3, 4 and 5 are additional isolated views, illustrating in sequence, how the sanitary cover is positioned on the dentist's overhead light handgrip.

In dental procedures, a dentist is assisted by an overhead light that is maneuvered by hand using a handgrip 10. To prevent possible transmission of disease from one patient to another, after completion of a procedure on a patient, a sanitary cover, generally designated 12, is removed from the handgrip 10 and replaced by a new handgrip sanitary cover before treatment of the next patient. For the use described, the sanitary cover 10 must be easy to remove but, equally and perhaps even more so, easy to install.

Sanitary cover 10 according to the present invention is, in essence, a bag in configuration, fabricated of clear plastic material from an initial work-in-process strip 14 having a linear expanse 16 and in parallel relation therealong a first edge 18 and a second edge 20 in widthwise spaced apart relation on opposite sides of the strip 14, the spacing therebetween delimiting a width expanse 22. A longitudinally oriented reference line establishes a medial fold line 24 separating the strip 14 into a work-in-process bag front panel 26 extending to the first edge 18 and a work-in-process bag rear panel 28 extending to the second edge 20, During the fabrication by heat sealing of the strip 14, it is pulled in a machine direction 30 past a printing station and imprinted along edge 20 with an inwardly pointed directional arrow 32, or another appropriate symbol, at spaced apart sites 34, the spacing between being correlated to the size 36 of the width of the rear panel 28 so that the imprint occurs at spaced intervals in the approximate middle of the top edge 38 of the rear panel 28.

Next, a folder folds the strip 14 in half along the fold line 24, as noted at 40, providing a work-in-process front and rear bag panels upon each other and, to be noted, the positioning of the edges 18 and 20 in confronting relation of one upon the other.

Following the positioning of the edges 18, 20, selected partial application of a heat seal 42, according to well understood techniques, is applied along the linear expanse 16 except for blocked out length portions in leading relation 44 and trailing relation 46 to the sites of imprinting 34, which in a preferred embodiment is a distance 48 of approximately two inches and constitutes the size of the opening 50 into the interior of the bag compartment 52 of the sanitary cover 12.

Spaced apart combination heat sealing and plastic severing means successively applied, as at 54, transversely along the strip linear expanse 16 completes the manufacture of the bag-configurated sanitary cover 12.

Figure 4:
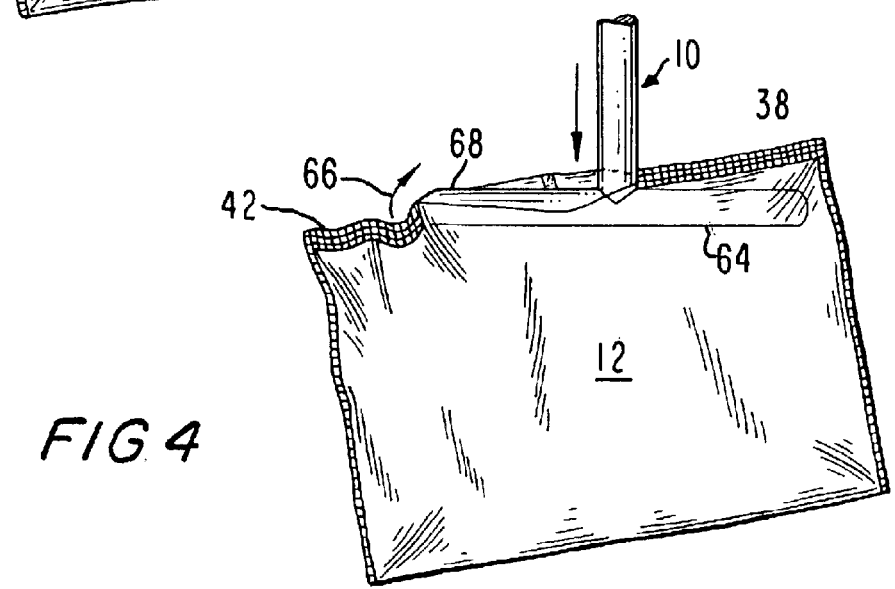
Figure 5:
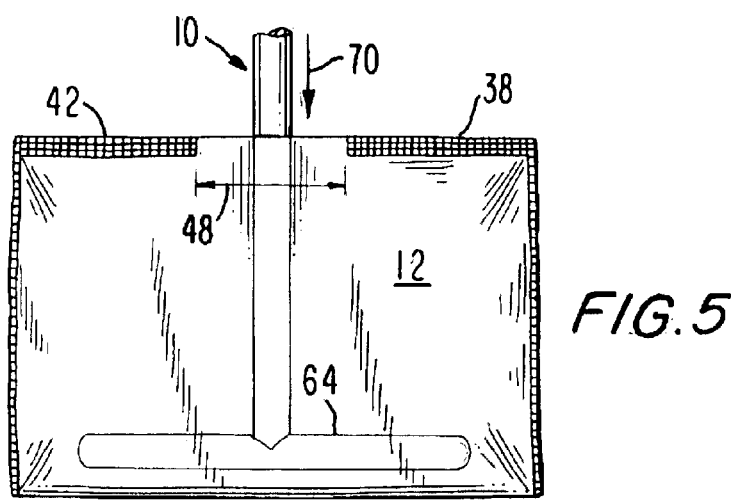

As best understood from FIG. 2, the arrow 32, or other symbol observed through the clear plastic front panel 26 is provided as finger grips for fingers 56 and 58 to be placed on opposite sides of the panels 26 and 28 and when rubbed, is effective to project the unsealed length portions of the edges 18, 20 into the opening 50, as depicted by the arrows 60, 62. This greatly facilitates initial placement of the one end 64 of handgrip 10 into the sanitary cover 12, as illustrated in FIG. 3, followed by the covering 66 of the other end 68 (FIG. 4) and the final movement 70 into the bag compartment of the sanitary cover 12 (FIG. 5). As known from common experience, thin gauge plastic often takes on a static electricity charge, and the rubbing preparation of FIG. 2 has been found in practice to neutralize this phenomena.

While the sanitary cover herein shown and disclosed in detail is fully capable of attaining the objects and providing the advantages hereinbefore stated, it is to be understood that it is merely illustrative of the presently preferred embodiment of the invention and that no limitations are intended to the detail of construction or design herein shown other than as defined in the appended claims.

What is claimed is:

1. A bag having an operative position serving as a sanitary cover of a handgrip of a dentist's overhead light constituted as an article of manufacture of clear pliable plastic sheet material comprising:

A. a strip of said clear plastic material delimiting a linear expanse having in parallel relation therealong a first edge and a second edge in widthwise spaced apart relation on opposite sides of said strip and delimiting a width expanse between said edges;

B. a longitudinally oriented reference medial fold line along said strip delimiting on opposite sides thereof a work-in-process bag front panel extending from said medial fold line to said first edge and a work-in-process bag rear panel extending from said medial fold line to said second edge;

C. an inwardly pointed directional arrow at spaced apart sites of imprinting along said rear panel at said second edge;

D. a folding in half of said strip along said fold line providing a work-in-process superposed relation of said bag front panel upon said bag rear panel and said second and first edges thereof in confronting relation of one upon the other;

E. selected partial application of a heat seal along said strip confronting second and first edges;

F. said selected extent of partial heat seal application being along said second and first edges and devoid of length portions in leading and trailing relation to said sites of imprinting for a total of approximately two inches; and G. spaced apart heat sealing and plastic-severing means successively applied transversely along said linear expanse to complete manufacture of said bag;

whereby rubbing between a thumb and fingers by a user externally of an observed arrow separates said unsealed confronting edges of said front and rear panels into a condition bounding an opening into said bag to facilitate providing said operative position of said bag in covering relation upon said overhead light handgrip.

2. A bag having an operative position serving as a sanitary cover of a handgrip of a dentist's overhead light constituted as an article of manufacture of clear pliable plastic sheet material comprising:

A. a strip of said clear plastic material delimiting a linear expanse having in parallel relation therealong a first edge and a second edge in widthwise spaced apart relation on opposite sides of said strip and delimiting a width expanse between said edges;

B. a longitudinally oriented reference medial fold line along said strip delimiting on opposite sides thereof a work-in-process bag front panel extending from said medial fold line to said first edge and a work-in-process bag rear panel extending from said medial fold line to said second edge;

C. an imprinted display symbol at spaced apart sites of imprinting along said rear panel at said second edge;

D. a folding in half of said strip along said fold line providing a work-in-process superposed relation of said bag front panel upon said bag rear panel and said second and first edges thereof in confronting relation of one upon the other;

E. selected partial application of a heat seal along said strip confronting second and first edges;

F. said selected extent of partial heat seal application being along said second and first edges and devoid of length portions in leading and trailing relation to said sites of imprinting for a total of approximately two inches; and G. spaced apart heat sealing and plastic-severing means successively applied transversely along said linear expanse to complete manufacture of said bag;

whereby rubbing between a thumb and fingers by a user externally of an observed imprinted symbol separates said unsealed confronting edges of said front and rear panels into a condition bounding an opening into said bag to facilitate providing said operative position of said bag in covering relation upon said overhead light handgrip.

* * * * *